US010518020B2

(12) United States Patent
Min et al.

(10) Patent No.: US 10,518,020 B2
(45) Date of Patent: Dec. 31, 2019

(54) SYSTEMS AND METHODS FOR PERFORMING ONLINE EXTRACORPOREAL PHOTOPHERESIS

(71) Applicant: Fenwal, Inc., Lake Zurich, IL (US)

(72) Inventors: Kyungyoon Min, Kildeer, IL (US); Katherine Radwanski, Des Plaines, IL (US)

(73) Assignee: Fenwal, Inc., Lake Zurich, IL (US)

( * ) Notice: Subject to any disclaimer, the term of this patent is extended or adjusted under 35 U.S.C. 154(b) by 68 days.

(21) Appl. No.: 15/656,152

(22) Filed: Jul. 21, 2017

(65) Prior Publication Data
US 2017/0319775 A1 Nov. 9, 2017

Related U.S. Application Data

(63) Continuation of application No. 15/189,752, filed on Jun. 22, 2016, now Pat. No. 9,744,288, which is a (Continued)

(51) Int. Cl.
*A61M 1/36* (2006.01)
*A61M 1/34* (2006.01)
(Continued)

(52) U.S. Cl.
CPC ............ *A61M 1/3681* (2013.01); *A61M 1/30* (2013.01); *A61M 1/3455* (2013.01);
(Continued)

(58) Field of Classification Search
CPC .... A61M 1/3496; A61M 1/3681–3686; A61M 1/3693
See application file for complete search history.

(56) References Cited

U.S. PATENT DOCUMENTS 4,321,919 A * 3/1982 Edelson .............. A61M 1/3681
128/898
4,568,328 A 2/1986 King
(Continued)

FOREIGN PATENT DOCUMENTS

EP 1066842 A2 1/2001
EP 0951305 B1 10/2004
(Continued)

OTHER PUBLICATIONS

David Peritt, "Potential Mechanisms of Photphersis in Hematopoietic Stem Cell Transplantion", Biology of Blood and Marrow Transplantion, vol. 12, p. 7-12, 2006.
(Continued)

*Primary Examiner* — Benjamin J Klein
(74) *Attorney, Agent, or Firm* — Cook Alex Ltd.

(57) ABSTRACT

Systems and methods for performing online extracorporeal photopheresis of mononuclear cells are disclosed. Whole blood is removed from a patient and introduced through a processing set into a separation chamber to separate the desired cell population from the blood. The separated cell population is processed through the set which is associated with a treatment chamber where the cells are treated. Once treated, the cells are returned to the patient. The processing set remains connected to the patient during the entire ECP treatment procedure and provides an online, sterile closed pathway between the separation chamber and the treatment chamber.

7 Claims, 5 Drawing Sheets

Related U.S. Application Data continuation of application No. 13/733,607, filed on Jan. 3, 2013, now Pat. No. 9,399,093.

(60) Provisional application No. 61/649,438, filed on May 21, 2012, provisional application No. 61/591,596, filed on Jan. 27, 2012.

(51) Int. Cl.
*A61M 1/30* (2006.01)
*B04B 11/02* (2006.01)

(52) U.S. Cl.
CPC ........ *A61M 1/3496* (2013.01); *A61M 1/3683* (2014.02); *A61M 1/3686* (2014.02); *A61M 1/3692* (2014.02); *A61M 1/3693* (2013.01); *A61M 1/3696* (2014.02); *B04B 11/02* (2013.01)

(56) References Cited

U.S. PATENT DOCUMENTS

| | | | |
|---|---|---|---|
| 4,578,056 A | 3/1986 | King et al. | |
| 4,683,889 A | 8/1987 | Edelson | |
| 4,838,852 A | 6/1989 | Edelson et al. | |
| 5,104,373 A | 8/1992 | Davidner et al. | |
| 5,383,847 A | 1/1995 | Edelson | |
| 5,459,322 A | 10/1995 | Warkentin | |
| 5,951,509 A | 9/1999 | Morris | |
| 5,984,887 A | 11/1999 | McLaughlin et al. | |
| 5,985,914 A | 11/1999 | Zeldis et al. | |
| 6,027,657 A | 2/2000 | Min et al. | |
| 6,219,584 B1 | 4/2001 | Lee | |
| 6,245,570 B1 | 6/2001 | Grimm | |
| 6,267,925 B1 | 7/2001 | Pages | |
| 6,582,386 B2 | 6/2003 | Min et al. | |
| 6,793,643 B1 | 9/2004 | Briggs | |
| 6,986,867 B2 | 1/2006 | Hanley et al. | |
| 7,025,877 B1 | 4/2006 | de Gheldere et al. | |
| 7,433,030 B2 | 10/2008 | Waldo et al. | |
| 7,476,209 B2 | 1/2009 | Gara et al. | |
| 7,601,298 B2 | 10/2009 | Waldo et al. | |
| 7,727,523 B2 | 6/2010 | Edelson et al. | |
| 7,846,121 B2 | 12/2010 | Wuepper | |
| 7,850,634 B2 | 12/2010 | Briggs | |
| 8,057,418 B2 | 11/2011 | Korbling et al. | |
| 8,556,844 B2 | 10/2013 | Leonard | |
| 9,399,093 B2 * | 7/2016 | Min ........................ | A61M 1/30 |
| 9,744,288 B2 * | 8/2017 | Min ........................ | A61M 1/30 |
| 2004/0124157 A1 | 7/2004 | Briggs et al. | |
| 2004/0127841 A1 * | 7/2004 | Briggs ............... | A61K 41/0066 604/6.01 |
| 2009/0209898 A1 | 8/2009 | Briggs | |
| 2010/0189597 A1 | 7/2010 | Hlavinka | |
| 2010/0210989 A1 | 8/2010 | Macpherson et al. | |
| 2013/0178834 A1 | 7/2013 | Greenburg et al. | |
| 2013/0197419 A1 | 8/2013 | Min et al. | |
| 2013/0252227 A1 | 9/2013 | Min et al. | |
| 2014/0370491 A1 | 12/2014 | Radwanski | |
| 2015/0196706 A1 | 7/2015 | Radwanski et al. | |
| 2015/0359959 A1 | 12/2015 | Radwanski et al. | |
| 2016/0114095 A1 | 4/2016 | Radwanski | |

FOREIGN PATENT DOCUMENTS

| | | |
|---|---|---|
| WO | WO96/22117 A2 | 9/1996 |
| WO | WO99/02215 A1 | 1/1999 |

OTHER PUBLICATIONS

Paolo Perseghin, "Extracorporeal Photochemotherapy as a Challenging Treatment for Cutaneous T-Cell Lymphoma, etc.", Transfusion Medicine and Hemotherapy, vol. 35, p. 8-17, 2008, published online Dec. 21, 2007.

Camille E. Introcaso, MD, "Extracorporeal Photophersis", Medscape Reference Drugs, Disease & Procedures, May 9, 2011.

European Search Report, dated May 21, 2013, for Appln. No. 13152312.8, filed Jan. 23, 2013.

* cited by examiner

SYSTEMS AND METHODS FOR PERFORMING ONLINE EXTRACORPOREAL PHOTOPHERESIS

FIELD OF THE DISCLOSURE

The present disclosure relates to systems and methods for performing online extracorporeal photopheresis ("ECP"). More particularly, the present disclosure is directed to systems and methods for removing mononuclear cells from a patient, treating the removed cells and returning treated cells to the patient in a single "on-line" procedure utilizing a multifunctional apheresis device, an independent and separately housed device for irradiating cells with light and a disposable processing set that provides a sterile closed pathway between the apheresis device and the irradiation device.

BACKGROUND

Whole blood is made up of various cellular and non-cellular components such as red cells, white cells and platelets suspended in its liquid component, plasma. Whole blood can be separated into its constituent components (cellular, liquid or other), and the separated component can be administered to a patient in need of that particular component.

The administration of blood and/or blood components is common in the treatment of patients suffering from disease. Rather than infuse whole blood, it is more typical that individual components be administered to the patient(s) as their needs require. For example, administration (infusion) of platelets is often prescribed for cancer patients whose ability to make platelets has been compromised by chemotherapy. Infusion of white blood cells (i.e., mononuclear cells), after the cells have undergone some additional processing or treatment, may also be prescribed for therapeutic reasons including treatment of diseases that specifically involve the white blood cells. Thus, it is often desirable to separate and collect the desired blood component from whole blood and then treat the patient with the specific blood component. The remaining components may be returned to the donor or retained for other uses.

There are several diseases or disorders which are believed to primarily involve mononuclear cells, such as cutaneous T-cell lymphoma, organ allograft rejection after transplantation and autoimmune diseases such as rheumatoid arthritis, systemic sclerosis, among others.

Cutaneous T-cell lymphoma (CTCL) is a term that is used to describe a wide variety of disorders. Generally, CTCL is a type of cancer of the immune system where T-cells (a type of mononuclear cell) mutate or grow in an uncontrolled way, migrate to the skin and form itchy, scaly plaques or patches. More advanced stages of the disease also affect the lymph nodes. Therapeutic treatment options for CTCL have previously been limited. While chemotherapy has been utilized, this particular form of treatment also has many associated undesirable side effects, such as lowered resistance to infection, bleeding, bruising, nausea, infertility and hair loss, just to name a few.

Organ allograft rejection may be characterized as the rejection of tissues that are foreign to a host, including transplanted cardiac tissue as well as lung, liver and renal transplants. Immunosuppression drug therapy following transplantation is common. However, there are potential drawbacks including reoccurring infection due to the compromised competence of the immune system caused by this type of therapy.

Similarly, graft versus host disease (GVHD) is a complication that can occur after a stem cell or bone marrow transplant in which the newly transplanted material attacks the transplant recipient's body. The differences between the donor's cells and recipient's tissues often cause T-cells from the donor to recognize the recipient's body tissues as foreign, thereby causing the newly transplanted cells to attack the recipient. GVHD may complicate stem cell or bone marrow transplantation, thereby potentially limiting these life-saving therapies. Therefore, after a transplant, the recipient is usually administered a drug that suppresses the immune system, which helps reduce the chances or severity of GVHD, See Dugdale, David C., et al. "Graft-Versus-Host Disease," *MedlinePlus A.D.A.M Medical Encyclopedia*, Updated Jun. 2, 2010.

Autoimmune diseases, including rheumatoid arthritis (RA) and progressive systemic sclerosis (PSS), can be characterized by an overactive immune system which mistakes the body's own tissues as being a foreign substance. As a result, the body makes autoantibodies that attack normal cells and tissues. At the same time, regulatory T-cells, which normally function to regulate the immune system and suppress excessive reactions or autoimmunity, fail in this capacity. This may lead to among other things, joint destruction in RA and inflammation of the connective tissue in PSS.

Where existing therapies for treating one or more diseases may result in certain unintended side effects, additional treatment may be desired or required. One known procedure which has been shown to be effective in the treatment of diseases and/or the side effects of existing therapies involving mononuclear cells is extracorporeal photopheresis or "ECP". Extracorporeal photopheresis (also sometimes referred to as extracorporeal photochemotherapy) is a process that includes: (1) collection of mononuclear cells (MNC) from a patient, (2) photoactivation treatment of the collected MNC cells; and (3) reinfusion of the treated cells (MNC) back to the patient. More specifically, ECP involves the extracorporeal exposure of peripheral blood mononuclear cells combined with a photoactive compound, such as 8-methoxypsoralen or "8-MOP" which is then photoactivated by ultraviolet light, followed by the reinfusion of the treated mononuclear cells. It is believed that the combination of 8-MOP and UV radiation causes apoptosis or programmed cell death of ECP-treated T-cells.

Although the precise mechanism of action in ECP treatment (in the different disease states) is not fully known, according to early theories, it was believed that photoactivation causes 8-MOP to irreversibly covalently bind to the DNA strands contained in the T-cell nucleus. When the photochemically damaged T-cells are reinfused, cytotoxic effects are induced. For example, a cytotoxic T-cell or "CD8+ cell" releases cytotoxins when exposed to infected or damaged cells or otherwise attacks cells carrying certain foreign or abnormal molecules on their surfaces. The cytotoxins target the damaged cell's membrane and enter the target cell, which eventually leads to apoptosis or programmed cell death of the targeted cell. In other words, after the treated mononuclear cells are returned to the body, the immune system recognizes the dying abnormal cells and begins to produce healthy lymphocytes (T-cells) to fight against those cells.

In addition to the above, it has also been theorized that extracorporeal photopheresis also induces monocytes (a type of mononuclear cell) to differentiate into dendritic cells capable of phagocytosing and processing the apoptotic T-cell antigens. When these activated dendritic cells are re-infused into systemic circulation, they may cause a systemic cytotoxic CD8+T-lymphocyte-mediated immune response to the processed apoptotic T-cell antigens like that described above. It will be appreciated that other possible mechanisms of action may be involved in achieving the benefits that have been observed from the ECP treatment of mononuclear cells and the subsequent benefits to patients undergoing ECP based therapies.

More recently, it has been postulated that ECP may result in an immune tolerant response in the patient. For example, in the case of graft versus-host disease, the infusion of apoptotic cells may stimulate regulatory T-cell generation, inhibit inflammatory cytokine production, cause the deletion of effective T-cells and result in other responses. See Peritt, "Potential Mechanisms of Photopheresis in Hematopoietic Stem Cell Transplantation," *Biology of Blood and Marrow Transplantation* 12:7-12(2006). While presently the theory of an immune tolerant response appears to be among the leading explanations, there exist other theories as to the mechanism of action of ECP relative to graft-versus-host disease, as well as other disease states.

Systems for performing ECP include, for example, the UVAR XTS Photopheresis System available from Therakos, Inc., of Exton, Pa. Further details of performing ECP on the Therakos system can be found, for example, in U.S. Pat. No. 5,984,887.

While the clinical benefits of ECP have been recognized, the use of ECP is not without its own drawbacks, including the systems and methods by which the ECP treatment is performed. For example, there are currently two commonly used methods for performing photopheresis—online and offline methods. In online methods, a dedicated photopheresis device, such as the Therakos device mentioned above, is used to perform the entire therapy including reinfusion of treated MNCs. Such devices are "dedicated" photopheresis devices, designed only for performing photopheresis and cannot perform other collection protocols needed in a hospital or blood processing setting including, for example, multifunctional apheresis protocols for collection of platelets, plasma, RBCs, granulocytes and/or perform plasma/RBC exchange protocols. In offline photopheresis methods, a multifunctional apheresis device may be used to collect mononuclear cells. The collected MNCs, typically contained in one or more collection containers, are severed or otherwise separated from the tubing set used during collection, where they are later treated in a separate irradiation or UVA light device followed by manual reinfusion of the treated cells to a patient. However, during such offline methods, when the cells are transferred from the apheresis device to the irradiation device (which device may be located in another room or laboratory) communication with the donor must be severed and accordingly, the cells detached from the donor. Thus, additional traceability procedures are required to insure that the treated MNC product is ultimately reinfused into the correct donor.

Therefore, it would also be desirable to develop "on line" systems and methods for providing ECP-treated mononuclear cells which avoids any additional product labeling and/or traceable handling requirements because the MNC product never leaves the disposable set which remains connected to the donor during the entire ECP treatment procedure. To this end, the systems and methods described herein include (1) a multifunctional automated apheresis device for harvesting MNCs from whole blood and reinfusing treated MNCs to a patient, (2) an irradiation device housed separately from the apheresis device which irradiates MNCs combined with 8-MOP to obtain treated MNC and (3) a disposable set which proves a sterile, closed pathway between the apheresis device and irradiation device and which remains connected to the patient during an entire photopheresis procedure. Use of a multifunctional apheresis device in accordance with the systems and methods described herein allows a hospital or medical facility to procure and maintain fewer apheresis devices, taking up less space and being more economical than having to acquire dedicated photopheresis devices used solely for performing ECP treatment, while also retaining a sterile closed pathway between two separate processing devices.

SUMMARY

In one aspect, the present disclosure is directed to an online extracorporeal photopheresis system. The system comprises a disposable fluid circuit comprising a processing chamber for separating whole blood into one or more components including mononuclear cells and at least one storage container adapted to receive mononuclear cells. At least a portion of the container is transparent to light of a selected wavelength. The system further comprises a separation device adapted to receive the processing chamber for effecting separation of mononuclear cells from whole blood and an irradiation device housed separately from the separation device adapted to receive the mononuclear cell storage container for treating the cells with a selected dose of light. The disposable fluid circuit provides a sterile closed pathway between the separation device and the irradiation device.

In another aspect, the present disclosure is directed to methods for performing an online extracorporeal photopheresis treatment procedure. The method comprises the steps of providing a disposable fluid circuit comprising a processing chamber for separating whole blood into one or more components including mononuclear cells and at least one treatment container adapted to receive mononuclear cells and separating from a source of whole blood a mononuclear cell product on an apheresis device adapted to receive the processing chamber for effecting separation of mononuclear cells from whole blood. The method further comprises combining the cell product with an activation agent and exposing the cell product to light in an irradiation device that is housed separately from the apheresis device to obtain a treated cell product. The treated cell product is then returned to the source and at least a portion of the fluid circuit remains connected to the source for the duration of the treatment procedure. The fluid circuit provides a sterile closed pathway between the separation chamber and the treatment chamber.

DESCRIPTION OF THE ILLUSTRATED EMBODIMENTS

The subject matter of the present disclosure relates generally to systems and methods for performing online extracorporeal photopheresis (ECP) treatment of mononuclear cells utilizing a multifunctional automated apheresis device, a disposable fluid circuit and an independent irradiation device housed separately from the apheresis device.

Figure 1:
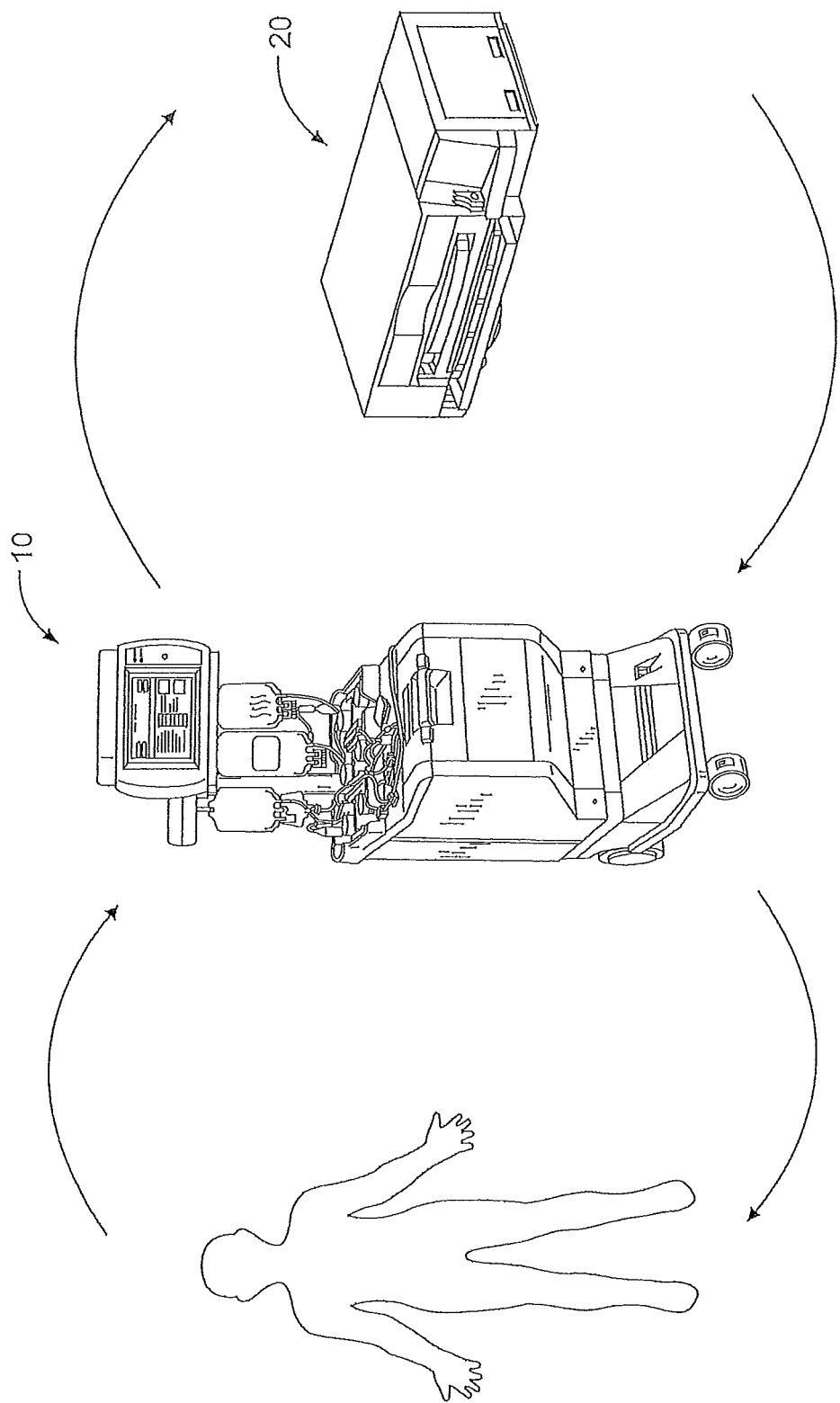
FIG. 1 is a diagram generally showing the mechanical components of a photopheresis treatment as described herein.
Figure 4:
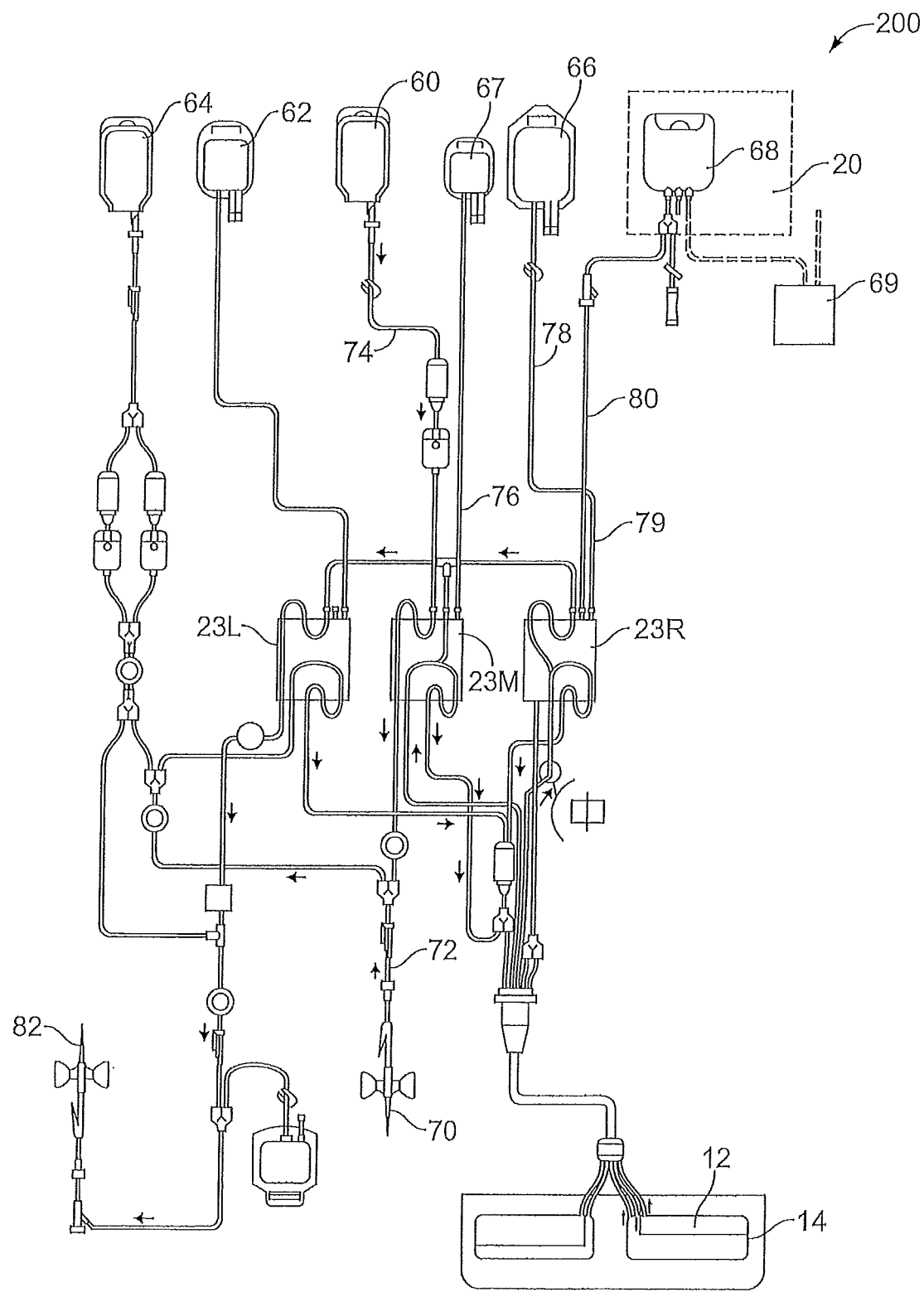
FIG. 4 is a diagram of the fluid circuit useful in the collection, treatment and reinfusion of mononuclear cells as described herein.

FIG. 1 shows, in general, the mechanical components that make up the system and that are used in the methods described herein. In accordance with the present disclosure, the system includes a separation component 10 and a treatment (i.e., irradiation) component 20. Preferably, irradiation component 20 is independent and housed separately from separation component 10. Although separately housed and independent devices, it is preferable that separation device 10 and irradiation device 20 are located adjacent to each other. In one example, separation device 10 and irradiation 20 may be located in the same room but physically spaced several feet or yards from each other. Irradiation device 20 may be on a table top located near or adjacent to separation component 10 allowing an operator or clinician to have access to both devices during a particular treatment procedure. In accordance with the systems and methods described herein a patient is connected to a blood processing set, i.e., fluid circuit 200. As generally illustrated in FIGS. 1 and 4, fluid circuit 200 provides a sterile closed pathway between separation component 10 and irradiation component 20. The system described herein also optionally includes a washing component which, preferably, is housed within the separation component. Preferably, the separation component 10 and washing component are one and the same, as will be described in greater detail below.

With reference to FIG. 1, whole blood is withdrawn from the patient and introduced into the separation component 10 where the whole blood is separated to provide a target cell population. In a preferred embodiment in accordance with the present disclosure, the target cell population may be mononuclear cells. Other components separated from the whole blood, such as red blood cells and platelets may be returned to the patient or collected in pre-attached containers of the blood processing set.

The separated target cell population, e.g., mononuclear cells, is then treated and irradiated in treatment component 20. As discussed above, in accordance with the present disclosure, treatment of mononuclear cells involves the photoactivation of a photoactive agent that has been combined with the mononuclear cells. Once treated, the mononuclear cells may optionally be provided to a washing component, which, as shown in FIG. 1, is housed within separation component 10 and, preferably, is one and the same. The treated mononuclear cells are separated from the supernatant and the concentrated cells may be returned to the patient. The supernatant liquid will typically include excess and unbound photoactivation agent. Optionally, the concentrated cells may further be combined with a suitable wash solution within separation/washing component 10. If washing of the treated mononuclear cells is performed, the suspension of mononuclear cells in a wash solution is then subjected to a centrifugal field (or other environment which can effect separation of the fluid components), whereby the mononuclear cells are concentrated and separated from the supernatant. The supernatant liquid may include any remaining unbound photoactivation agent. Supernatant may then be diverted to an appropriate waste container, while the treated mononuclear cells are returned to the patient, as generally shown in FIG. 1.

Apparatus useful in the collection (and washing) of mononuclear cells include the Amicus® Separator made and sold by Fenwal, inc., of Lake Zurich, Ill. Mononuclear cell collections using a device such as the Amicus® are described in greater detail in U.S. Pat. No. 6,027,657, the contents of which is incorporated by reference herein in its entirety. Preferably, the apparatus used for the harvesting, collection and reinfusion of mononuclear cells in accordance with the apparatus and methods described herein is a "multifunctional" automated apheresis device, as is the case with the Amicus® Separator. In other words, it is preferable that the separation component 10 be an multifunctional automated apparatus that can perform various collection protocols and/or serve multiple purposes, as may be needed by a particular hospital or facility, such that it can be used not only in the systems and methods for performing photopheresis treatment of MNC as described herein, but can also be used for other purposes including the collection of blood and blood components including platelets, plasma, red blood cells, granulocytes and/or perform plasma/RBC exchange, among other functions required by the hospital or medical facility. One benefit of the systems and described herein, in which a fluid processing circuit engages both a multifunctional apheresis device and an irradiation device, is that a "dedicated" photopheresis device that is designed only to perform ECP treatment, but which does not perform any other functions, is not required.

Figure 2:
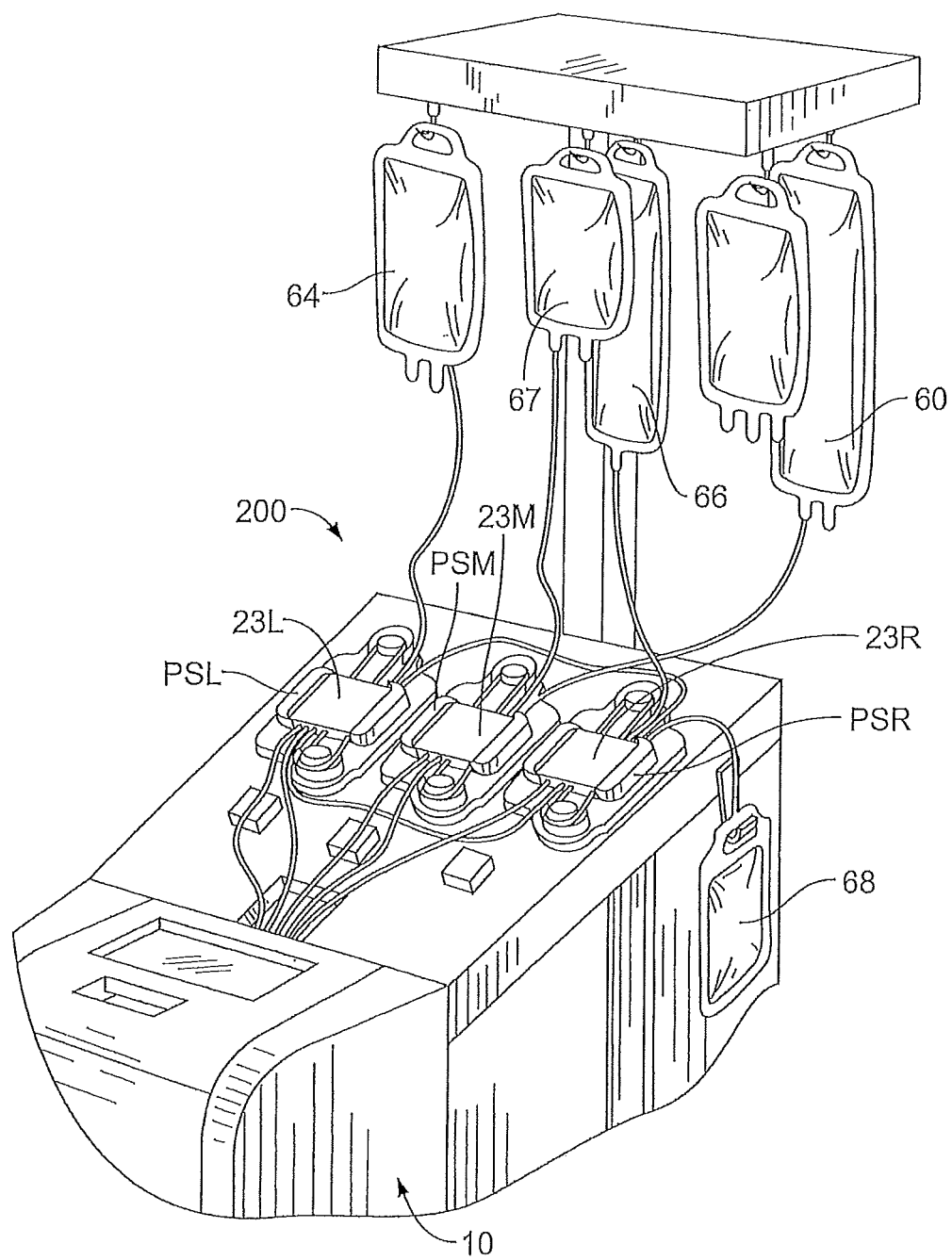
FIG. 2 is a partial perspective view of a multifunctional apheresis separator useful in the methods and systems described herein.
Figure 3:
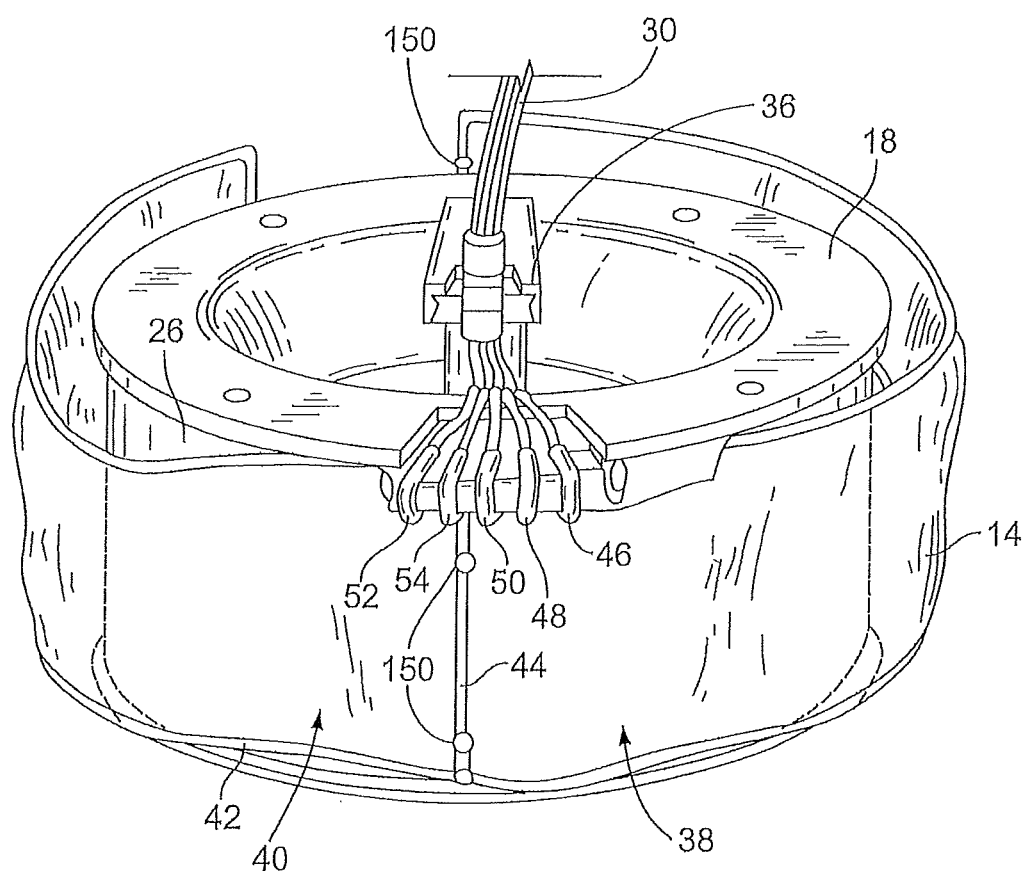
FIG. 3 is a perspective view of a processing container (separation chamber) of the processing set used with the separator of FIG. 2.

Briefly, FIGS. 2-4 show a representative blood centrifuge 10 with fluid circuit 200 mounted thereon (FIG. 2), the fluid circuit (FIG. 4) having a blood processing container 14 (see FIG. 3) defining a separation chamber suitable for harvesting mononuclear cells (MNC) from whole blood. As shown in FIG. 2, a disposable processing set or fluid circuit 200 (which includes container 14) is mounted on the front panel of centrifuge 10. The processing set (fluid circuit 200) includes a plurality of processing cassettes 23L, 23M and 23R with tubing loops for association with peristaltic pumps on device 10. Fluid circuit 200 also includes a network of tubing and pre-connected containers for establishing flow communication with the patient and for processing and collecting fluids and blood and blood components, as shown in greater detail in FIG. 4. As seen in FIGS. 2 and 4, disposable processing set 200 may include a container 60 for supplying anticoagulant, a waste container 62 for collecting waste from one or more steps in the process for treating and washing mononuclear cells, a container 64 for holding saline or other wash or resuspension medium, a container 66 for collecting plasma, a container 68 for collecting the mononuclear cells and, optionally, container 69 for holding the photoactivation agent.

In accordance with the methods and systems described herein, container 68 may also serve as the illumination container, and preferably, illumination container 68 is pre-attached to and integral with the disposable set 200. Alternatively, container 68 may be attached to set 200 by known sterile connection techniques, such as sterile docking or the like. In FIG. 2, container 68 is shown as suspended from device 10. However, container 68 may be housed within an adjacent separately housed irradiation device 20 (as shown by broken lines in FIG. 4), thereby eliminating the step of having the operator place container 68 into irradiation device 20. It will be appreciated that the tubing leading to and/or from container 68 in fluid circuit 200 is of a sufficient length to reach an irradiation device 20 that is adjacent to but housed separately from the separation device. In other words, regardless of whether container 68 is placed within irradiation device 20 prior to treatment or whether it is manually placed in device 20 during or after cells have been collected therein, the one or more lengths of tubing communicating with bag 68 as well as other tubing portions of fluid circuit 200 are preferably long enough to provide a sterile closed pathway between the two independent and separately housed separation device 10 and irradiation device 20 such that container 68 does not have to be separated or otherwise disconnected from the fluid circuit for cells collected therein to be treated in irradiation container 20.

With reference to FIG. 4, fluid circuit includes inlet line 72, an anticoagulant (AC) line 74 for delivering AC from container 60, an RBC line 76 for conveying red blood cells from chamber 12 of container 14 to container 67, a platelet-poor plasma (PPP) line 78 for conveying PPP to container 66 and line 80 for conveying mononuclear cells to and from separation chamber 14 and collection/illumination container 68. As will be known to those of skill in the art, the blood processing set includes one or more venipuncture needle(s) for accessing the circulatory system of the patient. As shown in FIG. 4, fluid circuit 200 includes inlet needle 70 and return needle 82. In an alternative embodiment, a single needle can serve as both the inlet and outlet needle.

Fluid flow through fluid circuit 200 is preferably driven, controlled and adjusted by a microprocessor-based controller in cooperation with the valves, pumps, weight scales and sensors of device 10 and fluid circuit 200, the details of which are described in the previously mentioned U.S. Pat. No. 6,027,657.

In accordance with the present disclosure, the fluid circuit is further adapted for association with the treatment component (i.e., irradiation device) 20. Apparatus for the irradiation of the mononuclear cells are also known and are available from sources such as Cerus Corporation, of Concord, Calif. One example of a suitable irradiation device is described in U.S. Pat. No. 7,433,030, the contents of which is likewise incorporated by reference herein in its entirety. As shown and described in U.S. Pat. No. 7,433,030, irradiation device preferably includes a tray or other holder for receiving one or more containers during treatment. Other irradiation devices may also be suitable for use with the method and system described herein, including devices available from Macopharma and/or Vilber Lourmet.

As noted above, separation chamber 12 is defined by the walls of a flexible processing container 14 carried within an annular gap defined by a rotating spool element 18 and an outer bowl element (not shown). The processing container 14 takes the form of an elongated tube which is wrapped about the spool element 18 before use. The bowl and spool element 18 are pivoted on a yoke between an upright position and a suspended position, also not shown.

When upright, the bowl and spool element 18 are presented for access by the user. A mechanism permits the spool 18 and bowl elements to be opened so that the operator can wrap the container 14 about the spool element 18, as FIG. 3 shows. Pins 150 on the spool element 18 engage cutouts on the container 14 to secure the container 14 on the spool element 18. In operation, the centrifuge 10 rotates the suspended bowl and spool element 18 about an axis 28, creating a centrifugal field within the processing chamber of container 14.

The radial boundaries of the centrifugal field are formed by the interior wall of the bowl element and the exterior wall 26 of the spool element 20. The interior bowl wall defines the high-G wall. The exterior spool wall 26 defines the low-G wall. Further details of the mechanism for causing relative movement of the spool 18 and bowl elements as just described are disclosed in U.S. Pat. No. 5,360,542 entitled "Centrifuge With Separable Bowl and Spool Elements Providing Access to the Separation Chamber," which is also incorporated herein by reference.

Figure 5:
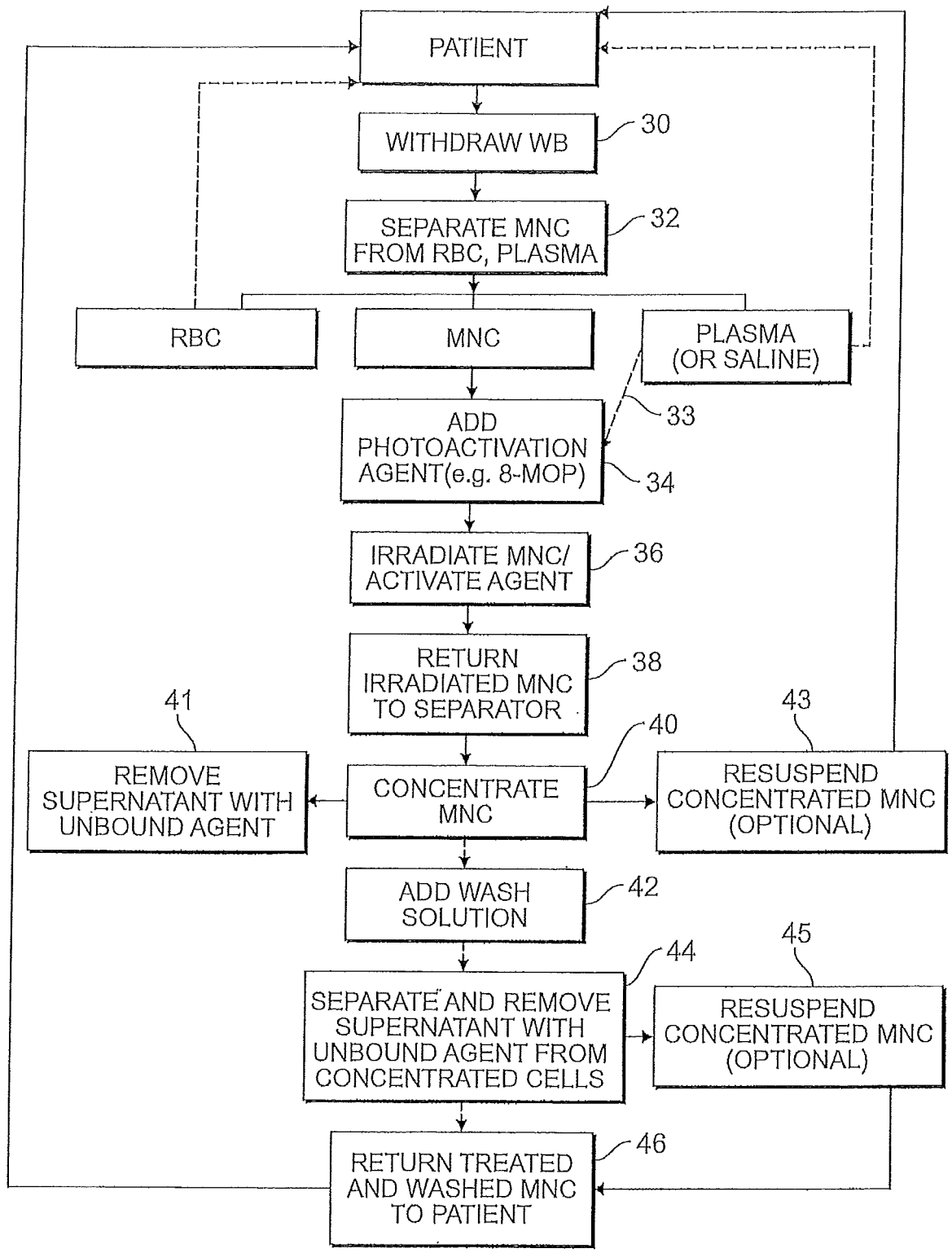
FIG. 5 is a flow chart setting forth the steps of the method of a photopheresis treatment as described herein.

Turning now to the method of treating mononuclear cells, as shown in FIG. 5, whole blood is withdrawn from a patient (step 30) through inlet needle 70 and introduced into the separation chamber 12 of container 14 of processing set 200, where the whole blood is subjected to a centrifugal field. The centrifugal field will separate the target cell population, i.e., mononuclear cells, from red blood cells, platelets and plasma (step 32). As discussed above, the components such as red blood cells and platelets may be returned to the patient or may be diverted to a container (e.g., container 67) for further processing.

Collection of the mononuclear cells may proceed in one or more cycles. The number of processing cycles conducted in a given therapeutic procedure will depend upon the total volume of MNC to be collected. For example, in a representative procedure, five collection cycles may be performed sequentially. During each cycle about 1500-3000 ml of whole blood can be processed to obtain a MNC volume of about 3 ml per cycle and a total volume of 15 ml of MNC. As shown in step 32 of FIG. 5, the final volume of mononuclear cells is then provided for further treatment in accordance with the present disclosure. Of course, the collection of MNC is not limited to the method described above. MNCs may be collected in any manner known to those of skill in the art, but preferably using a multifunctional apheresis device.

Effective treatment of the mononuclear cells with light may require that the amount of collected mononuclear cells have a suitable hematocrit. Thus, it may be desired or even necessary to dilute the mononuclear cells with a diluting solution such as plasma or saline, as shown in step 33. In the example described above, approximately 15 ml of MNC may be diluted in about 200 ml of plasma.

The diluted mononuclear cells (in container 68) are then combined with the suitable photoactivation agent in step 34. Alternatively, the desired volume of the agent may be pre-added to the container. As discussed above, for ECP treatment, the compound 8-methoxypsoralen (8-MOP) has been shown to be an effective photoactivation agent. However, other suitable photoactivation agents may be used, including, for example, a psoralen compound. In one example, the system, under the direction of the microprocessor-based controller, may be programmed to automatically deliver the desired amount of photoactive agent from, for example, container 69 before or after the MNC collection, based on the volume of MNC collected or to be collected. For example, 8-MOP may be pre-added to container 68 at the beginning of a particular procedure or alternatively, added to the MNCs collected in the container just prior to irradiation. The 8-MOP is combined with the collected and diluted mononuclear cells to arrive at a mixture having a final 8-MOP concentration of 200 nanograms/mL and/or any effective amount. Typically, the mononuclear cells may be combined with the photoactivation agent to arrive at a final 8-MOP concentration in a range of about 100 to 300 nanograms/mL. The 8-MOP or other photoactivation agent may be added directly to container 68 by a syringe through a port in the container, or added elsewhere in fluid circuit 200 also by a syringe.

As noted above, the mononuclear cells collected in accordance with the mononuclear cell collection process described above may be collected in container 68 that is suitable for irradiation by light of a selected wavelength. By "suitable" it is meant that the walls of the container are sufficiently transparent to light of the selected wavelength to activate the photoactive agent. In treatments using UVA light, for example, container walls made of ethylene vinyl acetate (EVA) are suitable. Accordingly, container 68 in which the mononuclear cells are collected may serve both as the collection container and the irradiation container. Container 68 may placed inside irradiation device 20 by the operator or more preferably, may be placed inside the irradiation chamber of irradiation device 20 at the beginning of the ECP procedure and prior to whole blood withdrawal (as shown by the broken lines representing device 20 in FIG. 4). In any event, container 68 preferably remains integrally connected to the remainder of fluid circuit 200 during the entire procedure, thereby maintaining the closed or functionally closed condition of fluid circuit 200.

As noted above, the fluid circuit 200 is adapted for association with the separation device 10 and with the treatment component (i.e., irradiation device) 20. It will be appreciated that the irradiation device does not have to be integral or even associated with the separation device 10. In fact, the irradiation device 20 is preferably an "adjunct" or independently housed irradiation device 20 used to perform the photopheresis therapy and located adjacent to or in a spaced-apart location from device 10, However, the disposable set 200 (including irradiation container 68) remains connected to the patient during the entire ECP treatment procedure and provides a sterile closed pathway between separation device 10 and the irradiation device 20.

Automated control of the MNC collection and the irradiation treatment may be effected by the microprocessor-based controller of the respective separation device 10 and irradiation device 20 with some operator input for each device. Alternatively, operation of both separation device 10 and irradiation device 20 and the process steps carried out by each may be remotely controlled by a separate controller (e.g., a computer) that communicates with both.

The mononuclear cells with photoactivation agent (8-MOP) are then irradiated for a selected period of time (step 36), In one non-limiting example, during treatment, the mononuclear cell product may be exposed to UV bulbs having a wavelength in the UVA range of about 320 nm to 400 nm for a selected period of time, such as approximately 10-60 minutes, resulting in an average UVA exposure of approximately 0.5-5.0 J/cm$^2$ and use preferably approximately 1-2 J/cm$^2$ or even more preferably approximately 1.5 J/cm$^2$ per lymphocyte.

Once treatment is complete, the treated mononuclear cells may be returned to separator 10 (and more specifically, the separation chamber 12 of container 14) as shown in step 38 of FIG. 5. For example, one of the pumps associated with cassette 23R may be actuated (automatically by the controller or under the manual control of the operator) to withdraw the treated MNC from container 68 and introduce the MNC into chamber 12 of container 14. Once inside chamber 12, the MNC may be concentrated (step 40). Supernatant, which will include unbound photoactivation agent is separated from the concentrated and treated cells and diverted to a waste container.

Concentrating treated MNCs prior to reinfusion allows for the concentrated cells to have a smaller total volume as compared to un-concentrated cells, and as a result, a smaller volume of concentrated MNCs may be reinfused to a patient faster. The concentrated cells may be resuspended in a suitable resuspension medium (e.g., plasma, saline) as shown in step 43 and returned to the patient. Optionally, prior to return to the patient, the concentrated and treated cells may be combined with a suitable wash solution (step 42), supplied (by the pumping action of pumps associated with cassette 23R) from containers 66 and/or 64 (see FIG. 4) is added to the concentrated cells.

Where the concentrated cells are optionally combined with wash solution (as per step 42), the mononuclear cells with wash solution within the chamber 12 (of container 14 of the disposable processing set 200) are subjected to a centrifugal field. The MNC are separated from remaining supernatant (step 44) under the field of centrifugal force. Any remaining unbound and excess photoactive agent will be separated from the concentrated mononuclear cells and suspended in the supernatant. The supernatant may then be withdrawn to a waste container 62 (FIG. 4) while the concentrated and washed mononuclear cells may be resuspended with a resuspension solution (such as, but not limited to, plasma or saline) as shown in step 45, and returned back to the patient, as shown in step 46 of FIG. 5. It will be appreciated that the step of washing the mononuclear cells may be repeated, as necessary. Solutions suitable for washing mononuclear cells include saline, plasma, or any other solution that is compatible with the mononuclear cell apheresis.

It will also be appreciated that the steps described above are preferably performed with the patient continuously connected to the system. In that regard, the entire treatment, including the washing of the MNC, is deemed to be an "on-line" procedure. Thus, in accordance with the systems and methods described herein, a multifunctional apheresis device 10, a disposable set 200 and an independent irradiation device 20 may be used to perform an online ECP treatment procedure. More specifically, a multifunctional apheresis device 10 is preferably used to collect MNCs from a patient and transfer the MNCs to an irradiation container 68 which is pre-attached or sterile connected to disposable set 200. MNCs combined with 8-MOP in container 68 are irradiated in device 20 resulting in treated MNCs. The treated MNC are conveyed through the disposable set 200 back into device 10 for reinfusion to the patient, all while at least a portion of the disposable set 200 remains connected to the donor, thus maintaining a closed "online" ECP treatment.

As previously mentioned, the online nature of the systems and methods described herein avoid the necessity for additional MNC product labeling or handling, as the mononuclear cells never leave the disposable set (and irradiation container 68 is never disconnected from the set) during the entire ECP treatment procedure. In other words, the disposable set 200 provides a sterile, closed pathway between the multifunctional apheresis device 10 and the irradiation device 20 such that from the time MNCs are harvested from the patient, to the time that the ECP treated MNCs are reinfused to the patient, an online closed system is maintained and reinfusion to the correct patient is ensured.

In a further embodiment, it may be desirable to cryopreserve at least a portion of fresh ECP treated and washed cells that remain after a selected volume (i.e., a single therapeutic dose) of treated cells are administered to a patient.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description.

The invention claimed is:

1. A method for treating a cellular product in a cell therapy comprising:
   a) collecting a desired cellular product from a source of a biological fluid including desired cells in a unitary disposable fluid circuit;
   b) determining a suitable hematocrit for the cellular product for effective treatment with light;
   c) combining said cellular product with saline or plasma in an amount to dilute said cellular product to the suitable hematocrit for said treatment within said fluid circuit;
   d) combining said cellular product with a photoactivation agent in an amount effective for said treatment within said fluid circuit;
   e) treating said cellular product to arrive at a treated product;
   f) introducing said treated product into a separation chamber of a separator;
   g) combining said treated product with a wash solution;
   h) separating said combination of treated product and wash solution within said fluid circuit to arrive at a concentrated treated product fraction and a supernatant fraction; and
   i) directing said concentrated treated product fraction through said fluid circuit to a patient.

2. The method of claim 1 comprising separating said treated product by centrifugation.

3. The method of claim 1 comprising diverting said supernatant fraction to a waste container.

4. The method of claim 1 wherein said cellular product is diluted with saline.

5. The method of claim 1 further comprising combining said treated product with biological fluid to obtain a combined treated product and biological fluid and separating mononuclear cells from said combined treated product and said biological fluid.

6. The method of claim 1 comprising collecting said treated product in a collection container.

7. The method of claim 1 in which 15 mL of cellular product is collected and diluted in 200 mL of plasma.

* * * * *